United States Patent [19]
Griffith

[11] 4,200,651
[45] Apr. 29, 1980

[54] URINE PRESERVATIVE COMPOSITION

[76] Inventor: Donald P. Griffith, 1200 Moursund, Houston, Tex. 77025

[21] Appl. No.: 972,799

[22] Filed: Dec. 26, 1978

Related U.S. Application Data

[63] Continuation of Ser. No. 824,612, Aug. 15, 1977, abandoned, which is a continuation-in-part of Ser. No. 769,693, Feb. 17, 1977, Pat. No. 4,042,337.

[51] Int. Cl.² .......................... A01N 9/20; A01N 9/24
[52] U.S. Cl. .................................. 424/320; 424/315; 424/324; 424/327
[58] Field of Search ................ 424/315, 324, 320, 327

[56] References Cited

PUBLICATIONS

Gale; C. A. vol. 64, 1966 10119h.
The Merck Index of Chemicals and Drugs 7th Ed. (1966) 1084–1085.
Nature; Hochstein; (10/2/65) vol. 208 pp. 46–48.

*Primary Examiner*—Allen J. Robinson
*Attorney, Agent, or Firm*—Arnold, White & Durkee

[57] ABSTRACT

The biochemical quality and characteristics of urine can be preserved by utilizing a combination of acetohydroxamic acid and benzyl (dodecyl carbamylmethyl) dimethyl ammonium chloride.

2 Claims, No Drawings

URINE PRESERVATIVE COMPOSITION

RELATED APPLICATIONS

This application is a continuation of application Ser. No. 824,612 filed Aug. 15, 1977, now abandoned, which is a continuation-in-part of U.S. application Ser. No. 769,693, filed Feb. 17, 1977 in the name of Donald P. Griffith, and issued Aug. 16, 1977 as U.S. Pat. No. 4,042,337.

BACKGROUND OF THE INVENTION

This invention relates to a preservative composition useful for stabilizing and preserving the biochemical characteristics of urine to enable testing and analysis thereof. More particularly this invention provides a preservative which may be added to human urine containing bacterial contamination resultant from infection to stabilize both pH and uric acid content of the urine for subsequent analysis.

Analysis of urine is often necessary in the diagnosis and treatment of urological disorders or infections. In such analyses, pH and uric acid content of the urine are frequently sought to be determined. However, if urine is permitted to stand at room temperature for a prolonged period of hours, the pH of the sample will frequently change as a result of the growth of bacterial infection present. Furthermore, uric acid concentration of the sample frequently changes upon standing as a result of a biochemical mechanism not completely understood.

It has been suggested that stabilization of uric acid in the sample might be effected by creating and maintaining an alkaline environment for the sample. However, it has been found that many standard alkaline materials either are not bactericidal or affect pH adversely. Stabilization of urine for analysis of minerals such as calcium, magnesium, phosphorus, sodium and potassium or for analysis of ammonia is accomplished using sulfamic acid. However, sulfamic acid does not stabilize pH or uric acid content.

Known germicidal compositions such as benzyl (dodecyl carbamylmethyl) dimethyl ammonium chloride have also been found ineffective when employed for this purpose.

SUMMARY OF THE INVENTION

In accordance with this invention there is provided a urine preservative composition which will maintain biochemical properties of urine contaminated with bacterial infection constant at room temperature for a period as long as several weeks. In particular, both pH and uric acid content of urine remains basically constant when the preservative of this invention is employed.

The preservative composition of this invention comprises a urologic bactericide, such as benzyl (dodecyl carbamethyl) dimethyl ammonium chloride (hereinafter called "benzyl" in this specification), and a source of hydroxamate groups such as acetohydroxamic acid.

This preservative composition is believed to preserve the urine by killing contaminating bacteria through the bactericide, inhibiting urease released by the dead bacteria through the presence of hydroxamate groups, and stabilizing uric acid by a mechanism which is not known. Urease is an intra-cellular enzyme released when bacteria are killed, and if the effect of the urease is not inhibited, the urine sample can become alkaline upon standing.

A discussion of the urease inhibiting effect of hydroxamate groups and compounds which may be used as a source of hydroxamate groups may be found in U.S. Pat. No. 4,024,256 and U.S. application Ser. No. 762,630, now abandoned, both in the name of Donald P. Griffith. Such disclosure is incorporated herein by reference.

The preservative composition of this invention may be effectively used in varying concentrations in urine, depending upon the extent of bacterial infection. In the presence of small concentrations of bacterial contaminants, i.e., less than $10^4$/milliliter, concentrations of the preservative composition as low as 0.1 milligram per milliliter of urine may be effective. Typically the preservative composition will be employed at concentrations of from about 0.3 to 3.5 milligrams per milliliter of urine for samples having typical bacterial concentrations. However, higher concentrations do not adversely affect the sample, and concentrations as high as 20 mg/ml may be used. Needed concentration of preservative will depend primarily upon concentration of bacterial contaminants. Sufficient benzyl is needed to kill all bacteria, and sufficient hydroxamate must be present to inhibit the urease released.

The preservative composition of this invention is comprised of approximately equal proportions by weight of the source of hydroxamate groups and the bactericide. Specifically, compositions comprising about 60 percent by weight acetohydrodroxamic acid and 40 percent by weight benzyl have been found effective. However, effective preservative compositions may be formulated by varing from these proportions so long as there is provided a sufficient amount of benzyl to kill bacterial contaminants in the urine and sufficient acetohydroxamic acid to inhibit urease from the dead bacteria. In general the preservative composition will comprise from about 25 to 75 percent by weight benzyl and 75 to 25 percent by weight acetohydroxamic acid.

The preservative composition of the invention exists in a powdered form and may be simply added to the urine sample soon after it is taken, or a measured sample of urine may be placed in a container with a small amount of preservative. The use of this preservative composition with a urine collection device is described in U.S. Pat. No. 4,042,337 filed in the name of Donald P. Griffith.

A number of potential pH stabilizing chemicals were tested to determine pH stabilizing effect on urine and results are shown in Table I. Measurements of pH were made, immediately following discharge, following adding of the preservative and a bacterial contamination and after 24 hours. Bacterial contamination in the amount of $10^6$/milliliter (proteus rettgeri) was added to these samples since the urine was collected from non-infected humans and frequently, therefore, was expected to be sterile.

A variance of greater than 0.1 in pH after 24 hours was taken as an indicator of pH instability since such a variance normally indicates that further variance will occur after prolonged standing.

TABLE I

| Preservative | Concentration | Bacteria Initial | Bacteria 24 hrs. | pH Bacteria & Initial | pH with pH Preservative | pH 24 hrs. | Comment |
|---|---|---|---|---|---|---|---|
| HCl (conc.) | .01 ml/ml | P. Rettgeri 10⁶/ml 10⁶/ml | Sterile | 6.5 | 2.5 | 1.8 | Too acidic |
| Chloroform | .02 ml/ml | " | 10⁷/ml | 6.5 | 6.5 | 8.4 | Not bactercidal |
| Chlorhexidine gluconate | .02 ml/ml | " | Sterile | 6.5 | 6.7 | 6.7 | Too alkaline |
| Phenyl mercuric nitrate | Crystals | " | 10⁶/ml | 6.5 | 6.5 | 6.8 | Not bactercidal |
| Formaldehyde 37% | .01 ml/ml | " | Sterile | 6.5 | 6.3 | 6.1 | Too acidic |
| Thymol | Crystals | " | 10⁶/ml | 6.5 | 6.5 | 7.8 | Not bactercidal |
| Potassium dichromate | Crystals | " | 10⁶/ml | 6.5 | 6.3 | 7.1 | Not bactercidal |
| Neosporin concentrate | .01 ml/ml | " | 10⁶/ml | 5.9 | 5.9 | 6.6 | Not bactercidal |
| Iodine - 20% | .05 ml/ml | " | Sterile | 5.8 | 3.4 | 3.1 | Too acidic |
| Iodine - 20% | .01 ml/ml | " | 10⁶/ml | 5.8 | 5.8 | 7.4 | Not bactercidal |
| Benzyl | 1 mg/ml | " | Sterile | 6.5 | 6.5 | 8.5 | Urease not inhibited |

Further tests were conducted with acetohydroxamic acid (AHA) alone, with benzyl alone, and with a 60/40 by weight mixture of AHA and benzyl as shown in Table II. The presence of both the benzyl and AHA gave consistent pH stabilization.

TABLE II

| Preservative | Concentration | Bacteria Initial | Bacteria 24 hrs. | pH Initial | pH with Bacteria & Preservative | pH 24 hrs. | pH 72 hrs. |
|---|---|---|---|---|---|---|---|
| AHA | 2 mg/ml | P. Mirablis 10⁶/ml | 10⁶/ml | 6.3 | 6.3 | 6.9 | 8.0 |
| AHA | 2 mg/ml | P. Rettgeri 10⁶/ml | 10⁶/ml | 6.3 | 6.3 | 6.7 | 8.1 |
| AHA | 3 mg/ml | P. Rettgeri 10⁶/ml | Sterile | 6.7 | 6.7 | 6.7 | 6.7 |
| AHA | 35 mg/ml | P. Rettgeri 10⁶/ml | Sterile | 6.7 | 6.7 | 6.5 | 6.5 |
| Benzyl | 1 mg/ml | P. Mirablis 10⁶/ml | Sterile | 7.0 | 7.0 | 8.7 | 8.9 |
| Benzyl | 1 mg/ml | P. Rettgeri 10⁶/ml | Sterile | 7.0 | 7.0 | 8.3 | 8.9 |
| Benzyl | 1 mg/ml | P. Morgani 10⁶/ml | Sterile | 6.5 | 6.5 | 8.5 | 8.8 |
| AHA & Benzyl | Low | P. Mirablis 10⁶/ml | Sterile | 5.75 | 5.75 | 5.70 | 5.75 |
| AHA & Benzyl | High | P. Mirablis 10⁶/ml | Sterile | 5.80 | 5.85 | 5.85 | 5.80 |
| AHA & Benzyl | Low | Klebsiella 10⁶/ml | Sterile | 5.75 | 5.75 | 5.70 | 5.65 |
| AHA & Benzyl | High | Klebsiella 10⁶/ml | Sterile | 5.80 | 5.80 | 5.80 | 5.80 |
| AHA & Benzyl | Low | P. Rettgeri 10⁶/ml | Sterile | 5.75 | 5.75 | 5.75 | 5.75 |
| AHA & Benzyl | High | P. Rettgeri 10⁶/ml | Sterile | 5.80 | 5.85 | 5.85 | 5.85 |

Low Concentration = AHA at 3 mg/ml & Benzyl at 2 mg/ml

Uric acid stabilization, when attempted by creating an alkaline condition in the urine using sodium hydroxide to create a pH of 8 to 9 showed that after one day reproducibility of the pH measurement when compared with an initial measurement was 97%, after two days reproducibility dropped to 91% and after five days reproducibility was only 75%.

To illustrate the uric acid stabilizing characteristics of the preservative of this invention, three urine samples were each divided into two specimens. One specimen of each was treated with the preservative of this invention the other was left untreated. Uric acid measurements were made after discharge and after five, eight, sixteen and sixty days. Results are shown in Table III.

TABLE III

| | Measured Uric Acid Concentration (mg/ml) | | | | |
|---|---|---|---|---|---|
| Sample | Initial | 5 Days | 8 Days | 16 Days | 60 Days |
| A w/preserv. | 87 | 83 | 82.5 | 82 | 87 |
| A w/o preserv. | 87 | 84 | — | — | 14 |
| B w/preserv. | 59 | 53 | 52 | 49 | 51 |
| B w/o preserv. | 59 | 55 | — | — | 4 |
| C w/preserv. | 50 | 45 | 42 | 41 | 43 |
| C w/o preserv. | 50 | 46 | — | — | 48 |

What is claimed is:

1. A bactericidal urine preservative composition capable of stabilizing pH and uric acid content of urine which comprises a mixture of from about 25 to 75 percent benzyl (dodecyl carbamylmethyl) dimethyl ammonium chloride and 75 to 25 percent acetohydroxamic acid.

2. A method of preserving the biochemical characteristics of pH and uric acid content in a urine sample which comprises adding to the urine a composition comprising (1) a bactericide comprising benzyl (dodecyl carbamylmethyl) dimethyl ammonium chloride in an amount sufficient to kill bacteria present in the sample and (2) acetohydroxamic acid in an amount sufficient to inhibit the urease produced by said bacteria, said composition comprising from about 25 to 75 percent of (1) and 75 to 25 percent of (2).

* * * * *